United States Patent [19]

Leung et al.

[11] Patent Number: 4,938,951
[45] Date of Patent: Jul. 3, 1990

[54] POTENTIATION OF TOPICAL COMPOSITIONS WHEREIN A UNIFORM MICRODISPERSION OF ACTIVE AGENT IS FORMED

[75] Inventors: Pak S. Leung, Highland Mills, N.Y.; Errol D. Goddard, Haworth, N.J.

[73] Assignee: Union Carbide Chemicals and Plastics Company Inc., Danbury, Conn.

[21] Appl. No.: 806,963

[22] Filed: Dec. 9, 1985

Related U.S. Application Data

[63] Continuation of Ser. No. 511,911, Jul. 8, 1983, abandoned, which is a continuation-in-part of Ser. No. 221,504, Dec. 30, 1980, abandoned.

[51] Int. Cl.$^5$ .................... A61K 7/42; A61K 31/74
[52] U.S. Cl. ........................................ 424/59; 424/80; 424/78; 424/60
[58] Field of Search .................... 424/78, 59, 60, 80

[56] References Cited

U.S. PATENT DOCUMENTS

| | | | |
|---|---|---|---|
| 2,435,005 | 1/1948 | Huppke et al. | 424/59 |
| 2,561,468 | 7/1951 | Guest | 424/60 |
| 3,146,170 | 8/1964 | Battista | 424/59 |
| 3,472,840 | 10/1969 | Stone | 536/43 |
| 3,485,915 | 12/1969 | Gerstein et al. | |
| 3,506,758 | 4/1979 | Epstein et al. | 424/60 |
| 3,529,055 | 9/1970 | Skoultchi et al. | 424/59 |
| 3,580,853 | 5/1971 | Parran, Jr. | 252/152 |
| 3,670,073 | 6/1972 | Shepherd et al. | 424/47 |
| 3,691,270 | 9/1972 | Charle et al. | 424/28 |
| 3,708,435 | 1/1973 | Starkman | 424/59 |
| 3,755,560 | 8/1973 | Dickert et al. | 424/78 |
| 3,784,488 | 1/1974 | Steinhauer et al. | 260/25 M |
| 3,821,363 | 6/1974 | Black et al. | 424/59 |
| 3,832,310 | 8/1974 | Grand | 252/543 |
| 3,864,473 | 2/1975 | Ciaudelli | 424/60 |
| 3,880,992 | 4/1975 | Smolin et al. | 424/60 |
| 3,895,104 | 7/1975 | Karg | 424/59 |
| 3,953,591 | 4/1976 | Snyder | 424/80 |
| 3,990,991 | 11/1976 | Gerstein | 424/70 |
| 3,992,336 | 11/1976 | Faucher et al. | 424/70 |
| 4,032,629 | 6/1977 | Osberghaus | 424/78 |
| 4,061,730 | 12/1977 | Kalopissus et al. | 424/59 |
| 4,096,240 | 6/1978 | Mathur | 424/59 |
| 4,115,547 | 9/1978 | Degen et al. | 424/60 |
| 4,129,645 | 12/1978 | Barnett et al. | 424/59 |
| 4,172,122 | 10/1979 | Kubik et al. | 424/59 |

FOREIGN PATENT DOCUMENTS

| | | |
|---|---|---|
| 0041654 | 12/1981 | European Pat. Off. |
| 2199971 | 4/1974 | France |
| 2268516 | 11/1975 | France |
| 8103849 | 5/1982 | South Africa |

OTHER PUBLICATIONS

Chemical Abstracts, vol. 90, No. 16, p. 364, cols. 1-2, Abstract No. 127,391s (Apr. 16, 1979); for Berger et al., "Design and Evaluation of Water Resistant Sunscreen Preparation".
J. Soc. Cosmet. Chem., vol. 29, No. 10, pp. 641-649 (1978); Fey, "Worterbuch der Kosmetik", Wissenschaftliche, Verlagagesellschaft mbH, Stuttgart, Fed. Rep. of Germany, p. 21 (1974).
The Merck Index, Ninth Edition, Merck & Co., Inc., Rahway, N.J., p. 1794, No. 1790 (1976).
Myddleton (Ed.), The Principles and Practice of Modern Cosmetics, Volume Two, Cosmetic Materials, Chemical Publishing Co., Inc., New York, pp. 120–129 (1967).
"GAF Guide to Cosmetics", Gaf Corp., New York (1967).
"Gantrez ® Monoester Resins", GAF Corp., New York (1967).
"Polymer JR for Skin Care", brochure #F-46628, Union Carbide Corp., Danbury, CT. (1977).
Stott et al., "Evaluation of a Polymeric Film-Forming Sunscreen Preparation in Tranqualized Hairless Mice", J. Soc. Cosmet. Chem., vol. 29, pp. 565–571 (Sep. 1978).
"Sunscreens", Amerchol Corp., Edison, N.J. (1979).
Technical Bulletins #A60-17-1, #A61-24-4A, #A6-2-30-2, #A60-18-5 and #A61-16-2, Van Dyk & Co., Inc., Belleville, N.Y., dated May 1977, Apr. 1978, Jun. 1978, Oct. 1977 and Apr. 1978, respectively.

Primary Examiner—Joseph L. Schofer
Assistant Examiner—Peter F. Kulkosky
Attorney, Agent, or Firm—Henry H. Gibson

[57] ABSTRACT

Topical, particularly light selective, compositions and methods using evaporative solvent, and a 0.5:1 to 20:1 ratio of film-forming polymer to topically active agent provide a microdispersion of agent in a polymer film exhibiting enhanced topical activity.

36 Claims, 2 Drawing Sheets

POTENTIATION OF TOPICAL COMPOSITIONS WHEREIN A UNIFORM MICRODISPERSION OF ACTIVE AGENT IS FORMED

CROSS REFERENCE TO RELATED APPLICATIONS

This application is a continuation of Ser. No. 511,911, filed July 8, 1983, now abandoned, which is a continuation-in-part of Ser. No. 221,504, filed Dec. 30, 1980 now abandoned.

BACKGROUND OF THE INVENTION

1. Field of the Invention

The instant invention relates to improved topically applied compositions comprising evaporative solvent, topically active agent and film-forming polymer. Preferred topically active agents are radiation selective, such as ultraviolet light-absorbing, materials.

2. Description of the Prior Art

The use of topically applied compositions finds application in numerous areas ranging from cosmetic preparations and anesthetics to insecticides and dyes. The varied use of topically applied agents has led to intense interest in minimizing the amount of agent employed for a particular application while yet achieving the same desired effect. As a result of this intense interest, the search for ways to improve the effect of a fixed amount of topically active agent has been of prime importance in all areas wherein topically active agents are employed. An example of this interest may be found in the prior art relating to sunscreening compositions.

The use of sunscreening compositions is required by a large segment of society since only a small portion of those exposed to sunlight have the natural pigmentation which provides protection against the harmful effects of solar radiation. Because of this propensity of many people to easily show erythema under prolonged exposure to sunlight, there is a need for sunscreening compositions to protect against erythema-causing radiation, i.e., ultraviolet radiation in the region of 260 to 320 nanometers, so that longer exposure to the sunlight with less risk of sunburn is possible.

A variety of sunscreening compositions are known in the art. One tendency in formulating sunscreening compositions has been to prepare compositions which are water-resistant or "substantive" to the skin, e.g., by chemically modifying the ultraviolet absorber to increase its interaction with the skin by quaternizing imidazoles as described in U.S. Pat. No. 3,506,758; by copolymerizing ultraviolet light absorbing monomers with other monomers to form water-resistant films (see, for example U.S. Pat. Nos. 3,529,055 and 3,864,473); or by forming polymeric films with water-insoluble polymers (e.g. see U.S. Pat. No. 3,784,488).

The use of the acid form of crosslinked ethylene-maleic anhydride copolymers to retain ultraviolet light absorbers is disclosed in U.S. Pat. No. 3,821,363. The use of water insoluble acrylate polymer having a solubility parameter of 6 to 10 in weak hydrogen bonding solvents is disclosed in U.S. Pat. No. 4,172,122. The use of water-insoluble, alcohol-soluble, film-forming polyamide materials is disclosed in U.S. Pat. No. 3,895,104 solely for the purpose of providing improved substantivity.

The sunscreening compositions of the prior art have not heretofore utilized film-forming polymers to enhance the intrinsic efficiency of topically applied agents with which they are employed, although varied uses, as above described have occurred. Thus, the purpose of employing polymers or polymeric materials in the compositions of the prior art has been directed solely towards improving the adherency, i.e., substantivity, of the topical material to the skin or have been employed solely as thickening agents.

The use of film-forming polymers has been suggested as being beneficial in potentiating sunscreens. In the brochure entitled "Polymer JR for Skin Care" by Union Carbide Corporation (dated June 1977) it is disclosed that a solution containing Polymer JR (a trademark of Union Carbide Corporation and hereinafter described) and two sunscreens (homomenthyl salicylate and p-amino benzoic acid (PABA)) showed increased protection from erythema-causing radiation. The degree of enhancement in protection is minimal for the compositions employed (about 5% by weight p-amino benzoic acid and about 8% by weight homomenthyl salicylate in admixtures with about 1% by weight and 2% by weight, respectively, Polymer JR (hereinafter defined)).

Further, the use of polymers in hair care compositions has been widely suggested and, further, has been employed to increase particle deposition and retention of particulate substances on a surface (U.S. Pat. No. 3,580,853).

Although the aforementioned prior art disclosed the utility of polymers for a number of various purposes the prior art does not disclose the use of a film-forming polymer in conjunction with a topically applied agent wherein the ratio of film-forming polymer to topically active agent is from about 0.5:1 to about 20:1, preferably from about 1:1 to about 10:1 and most preferably from about 1:1 to 4:1, and wherein the topically active agent exhibits enhanced behavior as compared to the behavior of the topically active agent when employed in the absence of the film-forming polymer.

The compositions of this invention employ "film-forming polymers" to "potentiate" topically applied agents, e.g., ultraviolet light-absorbing materials, contained therewith. The improved effectiveness achieved by employing such film-forming polymers has not heretofore been disclosed or appreciated in the prior art.

The potentiation of topically applied agents provides for more effective and economical use of such materials. In particular, the invention provides improved sunscreening compositions having an effective amount of at least one ultraviolet light-absorbing material and an effective amount of a film-forming polymer wherein when employed in combination with the film-forming polymer the ultraviolet light-absorbing material exhibits improved sunscreening protection as compared to that observed when employed without such film-forming polymer.

DETAILED DESCRIPTION OF THE INVENTION

It has been found that the addition of one or more film-forming polymers in solution to a composition containing an evaporative solvent and a topically active agent which is to be directly applied to a surface significantly improves the effectiveness of a given amount of said topically active agent when the ratio of film-forming polymer to topically active agent is from about 0.5:1 to about 20:1, preferably from about 1:1 to about 10:1, and most preferably from about 1:1 to about 4:1. In particular, in sunscreening compositions, surprisingly, it has been found that the combination of a film-forming polymer and ultraviolet light-absorbing material provides a sunscreening composition that when applied to the skin is dry to the touch without loss of the effectiveness of the ultraviolet light absorbance of the ultraviolet light-absorbing materials. Further, it has been found that the addition of a film-forming polymer to an ultraviolet light-absorbing material has additional beneficial effects on the ultraviolet light-absorbing material in that peak absorbance of the material may be shifted to more favored wavelengths. Thus, the resulting sunscreening composition as applied to the skin may exhibit ultraviolet light absorbence superior to that exhibited by employing the ultraviolet light-absorbing material without a film-forming polymer.

The compositions of this invention contain evaporative solvents, topically active agents and film-forming polymers and provide enhanced effectiveness for a given amount of topically active agent employed. For example, the sunscreening compositions of this invention require substantially less ultraviolet light-absorbing material, as compared to commercial sunscreening compositions, so that generally less than about 3 percent by weight of the sunscreen composition will be ultraviolet light-absorbing material, preferably from about 0.1 to about 3.0%.

The term "potentiation" is used herein to describe the ability of a film-forming polymer to enhance the effective activity of an applied amount of topically active agent, e.g., ultraviolet light-absorbing materials. The measure of enhancement is based in general on the improved or increased activity of the topically active agent based on its anticipated use. The "potentiation", i.e., enhanced activity, is not believed to be due to a change in active capacity of a topically active agent per se, such as a change in the absorption coefficient of the ultraviolet light-absorbing material, but instead reflects an increased activity per unit mass of topically active agent which has been applied. The measure of enhancement for an ultraviolet light-absorbing material is determined by the ability of a given amount of ultraviolet light-absorbing material dried onto a surface to absorb a greater amount, i.e. transmit a lower amount, of ultraviolet light falling on that surface in the presence of the film-forming polymer than when said film-forming polymer is not present, i.e., effectively increase ultraviolet absorbance for a given amount of topical material.

The term "topically active agents" as used herein refers to agents which are applied to a given surface to provide a beneficial effect as a result of the activity of the material on said surface. Typical surfaces include, but are not limited to, human skin, plants, plastics, glasses and the like. The topically active agent may be either a solid or a liquid. Any topically active agent can be utilized within the present invention, which exhibits potentiation.

The term "topically active agent" includes, but is not limited to, insecticides, pesticides, ultraviolet light-absorbing materials, anesthetics, fungicides, antimicrobial agents, germicides, vitamins and the like.

A preferred class of topically active agents, comprising a preferred embodiment of the present invention, pertains to those agents whose activity or efficiency on a surface depends fundamentally on the homogeneity of the film down to a microscopic or submicroscopic scale. For instance, films of light absorbing agents should not contain a significant amount of "holes" larger than the wavelength of the radiation thay are designed to absorb. Preferably any "hole" present should be of molecular dimensions. A preferred embodiment characterizing this type of potentiation is for light-sensitive compositions in which the topically active agent is a radiation selective material spread as a substantially uniform, significantly hole-free film.

The term "ultraviolet light-absorbing material" (hereinafter "UV-absorbing material") as used herein refers in general to any compound or combination of compounds capable of absorbing ultraviolet light from about 200 to about 370 nanometers. The preferred UV-absorbing materials are those which are capable of absorbing ultraviolet light in the erythemal range from about 260 to about 320 nonometers which may be employed in sunscreening compositions intended for application to human skin. The preferred ultraviolet absorbance of these UV-absorbing materials is in the range 290 to 310 nanometers. UV-absorbing materials suitable for use in this invention include, but are not limited to, para-amino benzoic acid, ethyl ester of para-amino benzoic acid and other esters of para-amino benzoic acid, e.g., the glyceryl ester, esters of substituted para-amino benzoic acid, e.g., any iso-amyl or ethyl hexyl esters of para dimethyl aminobenzoic acid, the ethyl esters of para diethyl aminobenzoic acid and esters of paramethoxycinnamic acid, e.g., 2-ethoxy-ethyl ester, certain esters of salicylic acid, e.g., homo menthyl salicylate. certain benzophenone derivatives, e.g., 2-hydroxy-4-methoxy benzophenone or 2,2-dihydroxy-4-methoxyl benzophenone, mixtures thereof and the like.

The preferred UV-absorbing materials are those which are crystalline materials at below about 200° C. although liquid UV-absorbing materials may be employed. A particularly preferred class of UV-absorbing materials is para-amino benzoic acid (hereinafter PABA) and esters thereof.

In addition to the aforementioned UV-absorbing materials, this invention may permit, surprisingly, the use of materials having their absorption at the lower end of the range of 260 to 320 nanometers. Thus, when materials not generally as desirable as sunscreens are employed in combination with a film-forming polymer they may exhibit a shift in the range at which they absorb ultraviolet radiation so as to provide sunscreening compositions with an improved wavelength at which absorbance occurs. The shift in absorption from the lower end of the wavelength range, often into the preferred range of about 290 to about 310 nanometers, may permit the use of materials which are not traditionally used as UV-absorbing materials. These materials may also be substantially cheaper to use than conventional UV-absorbing materials.

The term "film-forming polymer" as used herein refers to film-forming polymers that possess the ability to provide some physical bonding, with the topically active agent through physical forces, e.g., dipole-dipole, hydrogen bonding, dipole-induced dipole and the like.

In addition, these film-forming polymers tend to form substantive films when applied to the various surfaces and this is particularly the case when applied to human skin.

Although the exact mechanism by which potentiation occurs is not known, it is believed to involve the formation of a uniform microdispersion of the topically active agent in the film-forming polymer as a polymeric film is cast on a given surface. It is believed that the film-forming polymer inhibits the agglomeration, e.g., crystallization, of the topically active agent during the evaporation of the evaporative solvent thereby forming a dried, cast film in which the topically active agent is in a highly dispersed state. In the case of a crystalline topically active agent the formation of a uniform microdispersion has been evidenced in some cases by the virtual absence of the melting point of the topically active agent when measured on collected fragments of dried film specimens of compositions of this invention (as measured by Differential Scanning Calorimetry (DSC)).

The choice of film-forming polymer is not narrowly critical and may comprise water soluble or water insoluble film-forming polymers. The film-forming polymer must be in solution with the evaporative solvent to provide for effective potentiation when the evaporative solvent is removed. The film-forming polymer may be completely or partially soluble in the solvent. However, if the film-forming polymer is only partially soluble, the concentration of the film-forming polymer should be below the saturation level so that all the film-forming polymer present is in solution. If the film-forming polymer is only partially soluble in the solvent, the saturation level must be sufficient, i.e., high enough, to provide at least the minimum weight ratio of polymer to topically active agent in solution.

Water soluble film-forming polymers may be cationic, anionic or nonionic polymers. It is preferred to employ water soluble polymers such as: cellulose derivatives, particularly quaternary nitrogen-containing cellulose ethers, hydroxyethyl cellulose, hydroxypropyl cellulose and hydroxyethyl alkali metal carboxylalkyl cellulose derivatives, and free acid hydroxyalkyl carboxyalkyl cellulose derivatives; polyvinyl alcohol; vinylpyrrolidone homopolymers and copolymers; polycarboxylic acid derivatives; polyacrylamides; vinyl methyl ether homopolymers and copolymers; ethylene oxide resins; and the like.

Water insoluble polymers suitable for this invention include, but are not limited to, water insoluble polyamide polymers; esters of polymeric carboxylic acids, e.g., polyacrylate polymers; polypropylene oxide and derivatives thereof; and the like.

The preferred quaternary nitrogen-containing cellulose ethers (hereinafter referred to as QNCC ethers) employed in the topical compositions of this invention are those described in U.S. Pat. No. 3,472,840, granted to Stone et al., on Oct. 14, 1969, which disclosure is incorporated by reference herein.

The preferred cellulose ether derivative from which the QNCC ethers described above are prepared include those which are water soluble, non-ionic, lower alkyl or hydroxyl alkyl substituted. Such derivatives include methyl cellulose, ethyl cellulose, and hydroxyethyl cellulose.

A particularly efficacious QNCC derivative for the purpose of this invention is available from Union Carbide under the code designation "Polymer JR." This polymer has a molecular weight within the range of from about 100,000 to about 3,000,000. Polymer JR is a cationic cellulose ether have the structure:

wherein $R_{Cell}$ is a residue of an anhydroglucose unit, wherein Y is an integer having values from about 50 to about 20,000 and wherein each R individually represents a substituent of the general formula:

wherein the m is an integer having values from 0 to 10, n is an integer having values from 0 to 3, p is an integer having a value from 0 to 10 and b is an integer having a value from 0 to 3. The average values per anhydroglucose unit are: n is from about 0.1 to about 0.5 and the sum m+p is from about 0.8 to about 2.

The preferred QNCC ethers for use in the practice of the instant invention are those having viscosities of 50 to 35,000 centipoises (cps.) at 25° C. in 2 percent by weight aqueous solutions, when measured by ASTM D-2364-65 (Model LVF Brookfield, 30 rpm Spindle No. 2). QNCC ethers which are particularly useful in the practice of this invention are those sold by Union Carbide Corporation under the trade designation JR-125, JR-400, and JR-30M, signifying a polymer of the type described having viscosities (2 percent solutions by weight) of about 125 cps., about 400 cps. and about 30,000 cps. respectively.

The term "polyethylene oxide" as used in the instant invention encompasses not only the homopolymer, poly(ethylene oxide), but also copolymers of ethylene oxide in which ethylene oxide is copolymerized with other alkylene oxides such as propylene oxide, butylene oxide, styrene oxide and the like and other comonomers copolymerizable with ethylene oxide including ethylene oxide having terminal groups as ethers or esters, e.g. stearates, and the like. These polymers may be water soluble or water insoluble.

Examples of hydroxyalkyl carboxyalkyl celluloses include hydroxyethyl carboxymethyl cellulose, hydroxyethyl carboxyethyl cellulose, hydroxymethyl carboxymethyl cellulose, hydroxypropyl carboxymethyl cellulose, hydroxypropyl carboxyethyl cellulose, hydroxypropyl carboxypropyl cellulose, hydroxybutyl carboxymethyl cellulose, and the like. The preferred alkali metal salts of these hydroxyalkyl carboxyalkyl celluloses are the sodium and the potassium derivatives.

The evaporative solvent may be any liquid in which the film-forming polymer is completely or substantially soluble and which will readily evaporate when used in compositions of the present invention. The evaporation characteristics of the evaporative solvent can usually be characterized based on the partial vapor pressure of such solvents. The partial pressure of evaporative solvents of the present invention will generally be greater than 1 preferably from about 10 mm to about 250 mm at 25° C. Table A sets forth the partial pressures of some typical evaporative solvents of the present invention, as compared with non-evaporative solvents, e.g. oil-based materials. The partial pressure of many compounds may be determined experimentally using standard procedures as reported in literature.

TABLE A

| Solvent | Reported[a] Vapor Pressure mm, Hg at | T, °C. | Calculated[b] Vapor Pressure at 25° C. (mm, Hg) | Evaporative |
| --- | --- | --- | --- | --- |
| Acetone | 100 | 7.7° | 220 | Yes |
| Butanol | 10 | 30° | 6 | Yes |
| Ethanol | 40 | 19° | 70 | Yes |
| Glycerol | 1 | 126 | <<1 | No |
| Hexadecane | 1 | 105° | <<1 | No |
| Isopropanol | 40 | 23.8° | 44 | Yes |
| Methanol | 100 | 21° | 120 | Yes |
| Water | 24 | 25° | 24 | Yes |

[a]Handbook of Chemistry and Physics, CRC Press, Inc., 61st ed., D-203-216 (1980)
[b]Extrapolated from reported values over range of temperatures.

Preferred evaporative solvents include water and lower alkanols, such as methanol and ethanol.

The concentration of topical active agent may vary but is generally from about 0.01 to about 10.0 percent by weight, preferably is from about 0.1 to about 5.0 percent by weight and most preferably from about 0.1 to about 3.0 percent by weight. The concentration of film-forming polymer is generally employed in an amount from about 0.01 to about 10.0 percent by weight, preferably is from about 0.1 to about 5.0 percent by weight and most preferably from about 0.1 to about 3.0 percent by weight.

The ratio of film-forming polymer to topically active agent is from about 0.5:1 to about 20:1, preferably from about 1:1 or 2:1 to about 4:1. It has been found that the use of such relative proportions of the topically active agent and film-forming polymer is important in obtaining a uniform microdispersion and the optimum potentiation of this invention.

When the topical material is an UV-absorbing material, sunscreening compositions of this invention generally contains from about 0.1 to about 5.0 percent by weight ultraviolet light-absorbing material, the preferred range being from about 0.1 to about 3.0 percent by weight and the most preferred range being from about 0.5 to about 2.0 percent by weight. The film-forming polymer is generally present in an amount from about 0.1 to about 10.0 percent by weight, preferably in the range from about 0.1 to about 3.0 percent by weight. The ratio of film-forming polymer to UV-absorbing material is generally from about 0.5:1 to about 20:1, preferably from about 1:1 to about 10:1, and most preferably from about 1:1 to 4:1.

Using the compositions of the present invention, a process for potentiating an applied amount of a topically active agent has been developed which comprises:

(1) directly applying a topical composition consisting essentially of an evaporative solvent and a film-forming polymer in solution with the solvent, the film-forming polymer in admixture with the topically active agent, wherein the weight ratio of the film-forming polymer to the topically active agent is from 0.5:1 to about 20:1, to a surface: and (2) evaporating off the solvent to form a substantially uniform microdispersion of the topically active agent in a dried film containing the film-forming polymer on said surface to provide potentiation of an applied amount of the topically active agent.

The product produced by such a process is a cast film from which the solvent had been evaporated comprising a substantially uniform microdispersion of a topically active agent in a film containing film-forming polymer wherein the weight ratio of the film-forming polymer to the topically active agent is from about 0.5:1 to about 20:1.

In addition, the compositions of the invention may additionally comprise a wide range of inert and active ingredients commonly employed in cosmetic, toiletries, and other preparations, and include perfumes, colorants, humectants, emollients, skin conditioners, solvents, propellants, pigments, fillers, diluents, depilatories, stabilizers, and the like.

Sunscreening compositions were prepared in accordance with this invention and were tested both in-vivo and in-vitro in ultraviolet (UV) absorption.

In carrying our the in-vivo study, a Rofin arc lamp 7823 system with a 150 W Xenon lamp was used as the UV source. The UV rays were focused by a glass lens of focal length 21 mm and were filtered by a two inch path length of water in a quartz cell to remove most infra-red radiation and to cut down the heat. A secondary filter (Schopp UG-5) was used to eliminate light with a wavelength longer than about 400 nm and shorter than about 240 nm. The energy of the UV output was calibrated with a thermopile supplied by the Eppley Laboratory. It was found that at 40 cm from the focus lens a 30 second irradiation time was the exposure needed to deliver three times the minimal erythemal dosage (MED). It was later found that irradiation from a 1 $cm^2$ circular opening at 30 cm from the focus lens for 30 seconds was most discriminating. In all the in-vivo studies, the sunscreen preparation was applied at a level of 5 microliter on 1 $cm^2$ skin.

In-vitro studies were carried out by measuring the UV absorbance of various sunscreening compositions of this invention after said same had been dried on planar quartz plates with a Beckman Acta V spectrometer.

Topical compositions were prepared according to this invention containing topically active agents comprising other than UV-absorbing materials. The compositions were examined by Differential Scanning Calorimetry (DSC) using a DuPont 900 Thermal Analyzer. A loss in crystallinity of the topically active agent observed in these compositions is consistent with the presence of these materials in a uniform microdispersion in the dry cast films.

In carrying out the several examples, hereinafter, the following film-forming polymers were employed:

CELQUAT L200 (CELQUAT is the Trade Mark of National Starch Corp.) is a quaternary ammonium cellulose derivative.

MERQUAT 100 (MERQUAT is the Trade Mark of Merck and Company, Inc. Rahway, N.J.) and CALGON 502 (CALGON is the Trade Mark of Calgon Corp.) are both polymers of N,N-dimethyl 3,5-methylene piperidinium chloride.

GAFQUAT-755 (GAFQUAT is the Registered Trade Mark of GAF Corporation) is a quaternary ammonium compound which is a copolymer of vinylpyrrolidone and dimethyl amino ethyl methacrylate quaternized with diethyl sulphate. The various GAFQUATS have molecular weights in the range of from about 100,000 to about 1,000,000 with GAFQUAT-755 having a molecular weight of about 1,000,000 (available as a 20% by weight aqueous solution);

POLYOX (POLYOX is the Trade Mark of Union Carbide Corporation) designates a group of very high molecular weight polymers of ethylene oxide (PEO).

CARBOWAX (CARBOWAX is the Trade Mark of Union Carbide Corporation) for polyethylene glycol polymers. CARBOWAX 6000 and CARBOWAX 20M are code names for polymers having molecular weights of about 6000 and 20,000, respectively;

METHOCEL (METHOCEL is the Trade Mark of Dow Chemical Corporation) are methyl ethers of cellulose, including hydroxypropyl methyl cellulose;

CELLOSIZE (CELLOSIZE is the Trade Mark of Union Carbide Corporation) is a hydroxyethyl cellulose.

CELLOSIZE (AP-300H) is a grade of hydroxyethyl cellulose polymer.

KESSCO PEO 6000 (KESSCO is the Trademark of Armour) is the Trade Mark for a group of polymers which are polyethylene glycol esters of fatty acids;

KLUCEL L (KLUCEL is the Trade Mark of Hercules Corporation) is a hydroxypropyl cellulose polymer;

Polyvinyl alcohol (PVA) (100 percent hydrolyzed) having a molecular weight of about 14,000, sold by Aldrich Chemical Company;

Polypropylene glycol (PPG 1025) having a molecular weight of about 1025, sold by Union Carbide Corporation;

GANTREZ (GANTREZ is the Trade Mark of GAF Corporation) is an ester of polymethyl vinyl ether of maleic acid; and CROTEIN Q (sold by Croda Corporation) is a cationic protein.

The compositions of the invention may be further illustrated by the following nonlimiting examples. Ingredients used in the compositions are identified by commercial designation as hereinbefore set forth.

EXAMPLE 1

To test the sunscreening compositions of this invention and the potentiating effect of water-soluble film-forming polymers on UV-absorbing materials the following experiment was carried out.

Four test cases were evaluated using para-amino benzoic acid and Polymer JR, as follows:

(1) Human skin was irradiated with Rofin Xenon lamp filtered radiation after the application of 5 microliter/cm$^2$ of 1% by weight of para-amino benzoic acid (PABA) in 50 percent ethanol;

(2) Human skin was irradiated with radiation, as in (1), after the application of 5 microliter/cm$^2$ of a solution containing 1 percent by weight Polymer JR and 1 percent by weight PABA in 50 percent ethanol;

(3) Human skin was irradiated, as in (1), with radiation through a Polymer JR filter (prepared by drying a 1 percent by weight Polymer JR solution on a quartz plate) after the application of 5 microliter/cm$^2$ of 1 percent by weight PABA to the skin; and (4) Human skin was irradiated with radiation, as in (1), through a filter prepared by applying 5 microliter/cm$^2$ of a solution containing 1 percent by weight Polymer JR and 1 percent by weight PABA in 50 percent ethanol on a quartz plate and drying it thereof.

Evaluation of the sunscreening solutions of Cases (1) and (3) (not of this invention) revealed that erythema was observed whereas, no sign of erythema was observed for Cases (2) and (4). Thus, when the sunscreening compositions of this invention were employed Cases (2) and (4) the UV-absorbing material clearly showed improved protection from erythema, i.e. potentiation of the topically active agent p-amino benzoic acid.

EXAMPLES 2-13

Sunscreening compositions prepared according to the invention were evaluated by in-vitro UV absorption studies by drying on a 3 cm$^2$ quartz plate 20 microliter solutions containing 0.5 weight percent PABA and a film-forming polymer. The UV-absorbing material selected herein was PABA. (The concentration of polymers as indicated by Polymer:PABA ratio in Table I).

Examples 2-13 of Table I show the potentiation achieved by employing various film-forming polymers with PABA when employed in a ratio of film-forming polymer to UV-absorbing material, of from about 0.5:1 to about 4:1. The UV absorbance of papa-amino benzoic acid when measured in the absence of a film-forming polymer, applied in 50 percent ethanol, after drying is 0.06.

The aforementioned compositions were examined by microscopy. The crystal formation of dried para-amino benzoic acid was observed to change when a film-forming polymer was employed. As compared to PABA, which is dried in the absence of a film-forming polymer, the addition of such a polymer led to a significant reduction in the degree of crystallinity of the dried PABA. Differential Scanning Calorimetry showed the melting point of PABA was substantially eliminated, consistent with the formation of a uniform microdispersion of UV-absorbing material.

Figure 2:
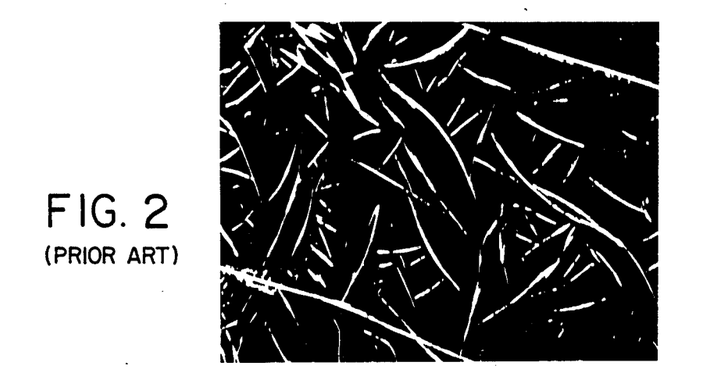
FIG. 2 is a photomicrograph of a topically active agent as used in the prior art.
Figure 3:
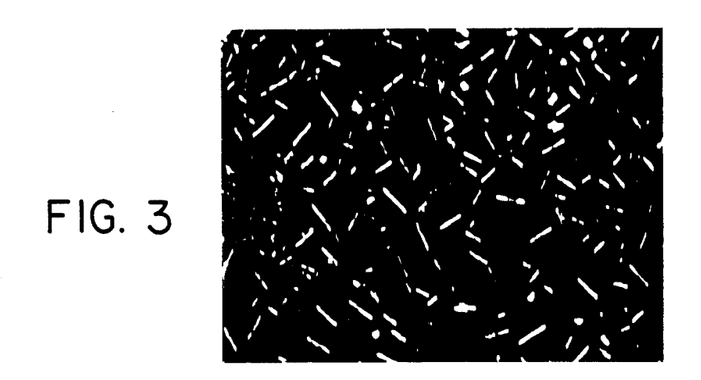
FIGS. 3 and 4 are photomicrographs of dried cast films produced by compositions of this invention.
Figure 4:
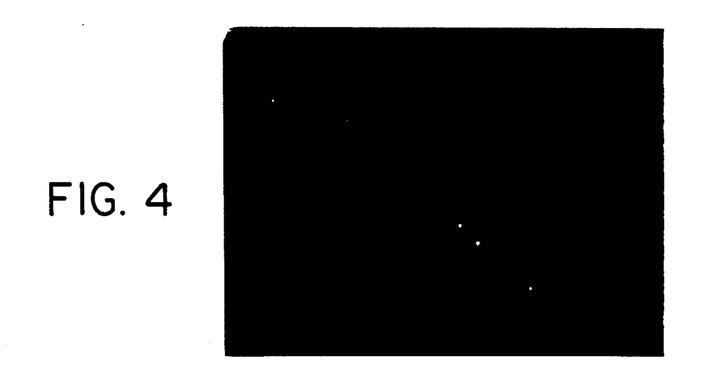

FIGS. 2-4 are photomicrographs (approximately 50×actual size) of in-vitro applications of topical compositions of 50% aqueous ethanol solution (as evaporative solvent) containing 0.5 wt.% PABA. The compositions were applied to and dried on planar quartz glass. FIG. 2 represents compositions of the prior art without filmforming polymer and exhibits substantial crystallization. FIG. 3 shows that crystallization is significantly reduced for an identical composition but which additionally contains 0.5 wt.% Polymer JR-400. As Example 12 demonstrates such compositions exhibit potentiation signifying the presence of a substantially uniform micro-dispersion of PABA between the remaining crystals. FIG. 4 is similar to FIG. 3 but contains 1.0 wt.% Polymer JR resulting in a substantial absence of crystallization and greater potentiation.

Figure 1:
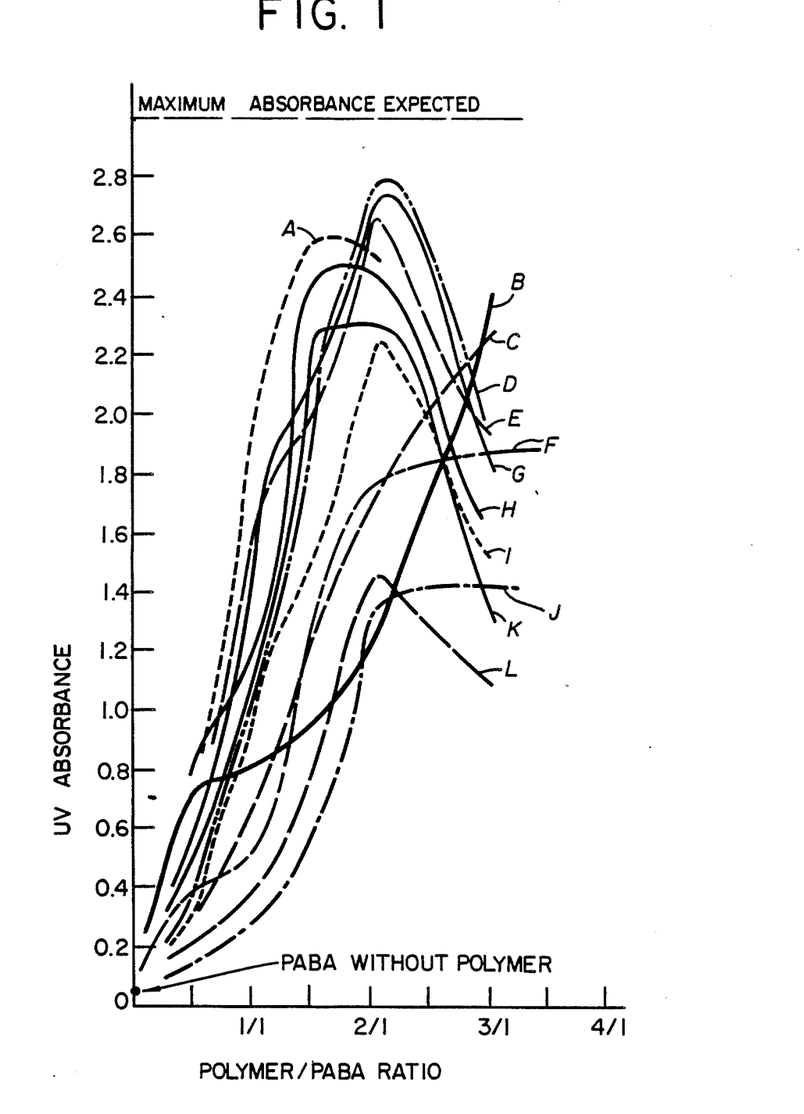
FIG. 1 is a graph showing the potentiated activity of compositions of this invention.

The results of Table I are graphically displayed in FIG. 1. The absorbance as a function of the ratio (by weight) of film-forming polymer to p-amino benzoic acid can be seen by reference to FIG. 1 wherein the letters A through L represent compositions containing the following film-forming polymers in admixture with p-amino benzoic acid:

| Letter in FIG. | Film-Forming Polymer |
| --- | --- |
| A | GAF QUAT 755N |
| B | PVA 1400 |
| C | MERQUAT 100 |
| D | CELLOSIZE (QP 300H) |
| E | JR 125 |

-continued

| Letter in FIG. | Film-Forming Polymer |
|---|---|
| F | KLUCEL L |
| G | PEO 20M |
| H | CELQUAT L200 |
| I | KESSCO PEO 600 (STEARATE) |
| J | CARBOWAX 6000 |
| K | JR 400 |
| L | PPG (1025) |

EXAMPLE 14

The effect on the peak wavelength at which an UV-absorbing material absorbs when cast as a dry film in the presence of a film-forming polymer was evaluated as a function of the pH of a composition containing a UV-absorbing material and a film-forming polymer.

A sunscreening composition according to the invention was prepared comprising $0.83 \times 10^{-3}$ percent by weight PABA and $0.83 \times 10^{-3}$ percent by weight Polymer JR-400. The UV absorbance of this composition was tested after adjusting the pH of the three samples of the composition such that the composition had a pH of 10.5, 8.1 and 4.1 (A 1 percent by weight solution of PABA (50 percent ethanol) has a pH of 4.2). The peak absorbance of these solutions was measured and showed absorbance at about 260 nm, about 265 nm and about 285 nm, respectively (measured in a 1 cm cell). To demonstrate this effect of drying of the solutions containing a UV-absorbing material and a film-forming polymer a second series of sunscreening composition were prepared comprising 0.5 percent by weight PABA and 0.5 percent by weight Polymer JR 400 in 50 percent ethanol. This series of samples was prepared having pH 10.5, 8.2 and 4.4. Twenty microliters of each applied to a quartz plate (3 cm$^2$) and dried. The peak absorbance of each sample was 260 nm, 270 nm and 295 nm respectively. Thus, a shift in the UV-absorbing material was observed upon formation of a dry film.

TABLE I (1.2)

| Example | Film-Forming Polymer (Polymer:PABA Ratio) | Absorbance (3,4) | | | | | |
|---|---|---|---|---|---|---|---|
| | | 0.5:1 | 1:1 | 1.5:1 | 2:1 | 3:1 | 4:1 |
| 2 | GAF QUAT 775N | 0.8 | 2.0 | 2.6 | 2.5 | — | — |
| 3 | PVA 1400 | 0.8 | -0.8 | 0.9 | 1.2 | 2.5 | — |
| 4 | MERQUAT 100 | 0.28 | 0.7 | 1.7 | 1.65 | 2.3 | — |
| 5 | CELLOSIZE (QP 300H) | 0.3 | 1.05 | 2.2 | 2.8 | 1.8 | — |
| 6 | JR 125 | 0.8 | 1.7 | 2.0 | 2.7 | 1.9 | — |
| 7 | KLUCEL L | 0.4 | 0.5 | 1.4 | 1.8 | 1.5 | — |
| 8 | PEO 20 M | 0.55 | 1.9 | 2.1 | 2.8 | 1.8 | — |
| 9 | CELQUAT L 200 | 1.0 | 1.1 | 2.5 | 2.5 | 1.5 | — |
| 10 | KESSCO PEO 6000 | 0.3 | 1.0 | 1.5 | 2.3 | 1.5 | — |
| 11 | CARBOWAX 6000 | — | 0.25 | — | 1.4 | — | 1.4 |
| 12 | JR 400 | 0.5 | 0.9 | 2.3 | 2.3 | 1.3 | — |
| 13 | PPG (1025) | 0.22 | 0.35 | 0.82 | 1.5 | 1.2 | — |

(1) Dry films cast from 20 microliters of a solution (50 percent ethanol containing 0.5 percent by weight PABA and polymer (concentration as indicated by ratio) on a planar quartz surface with an area of 3 cm$^2$
(2) Analysis by DSC showed a substantial loss of crystallinity of PABA and virtual elimination of the melting point of PABA with increasing ratio of film-forming polymer to PABA.
(3) Absorbance = $\log \frac{1}{(Transmittance)}$; measured at 296 nm.
(4) The absorbance of PABA; measured after drying PABA on a planar quartz surface, prepared by applying 20 microliters of a solution (50% ethanol containing 0.5% by weight PAPA) on a planar quartz surface having an area of 3 cm$^2$ was 0.06.

EXAMPLES 15–19

The effect on UV absorbance of PABA of a change in the molecular weight of the film-forming polymer was tested by preparing three sunscreening compositions according to this invention as follows:

(1) 0.5 percent by weight PABA and 1.0 percent of Polymer JR 125;
(2) 0.5 percent by weight PABA and 1.0 percent by weight Polymer JR 400; and
(3) 0.25 percent by weight PABA and 0.5 percent by weight Polymer JR 30M.

The aforementioned sunscreening compositions were evaluated for UV absorbance in the range from about 250 nm to about 320 nm with peak absorbancy being at about 296 nm. The measured ultraviolet light absorbance is shown in Table II.

TABLE II

| Example | PABA Conc.(2) | Polar Polymer | Polymer Conc. | Absorbance(1) |
|---|---|---|---|---|
| 15 | 0.5 | JR-125 | 1.0 | 2.5 |
| 16 | 0.5 | JR-400 | 1.0 | 2.3 |
| 17 | 0.25 | JR-30M | 0.5 | 1.2 |
| 18 | 5.0 | — | — | 0.1 |
| 19 | 1.0 | — | — | 0.06 |

(1) UV absorbance at 296 nm.
(2) Weight percent

Table II shows that the UV absorbance of the molecular weight of the sunscreening compositions changes little as a function of the molecular weight of the film-forming polymer. Further, Table II shows the marked increase in UV absorbance, as measured by in-vitro studies, of the sunscreening compositions of this invention over a 5.0 percent and a 1.0 percent by weight PABA solution (in 50 percent ethanol) when employed without film-forming polymer.

EXAMPLES 20–28

Sunscreening compositions were prepared according to this invention comprising 0.25 percent by weight ESCALOL 507, i.e. 2-ethyl hexyl para-dimethyl amino benzoate (ESCALOL 507 is the Trade Mark of Van Dyke Corporation) and from about 0.25 to about 1.25 percent by weight of a film-forming polymer, as shown in Table III.

TABLE III(1,2)

| Example | Film-Forming Polymer | Ratio of Polymer: ESCALOL | Absorbance |
|---|---|---|---|
| 20(3) | — | — | 0.08 |
| 21 | CELLOSIZE (QP 300H) | 1/1 | .15 |
| 22 | CELLOSIZE (QP 300H) | 2/1 | .15 |
| 23 | CELLOSIZE (QP 300H) | 3/1 | .15 |
| 24 | CELLOSIZE (QP 300H) | 4/1 | .15 |
| 25 | PEO (20M) | 1/1 | 1.35 |
| 26 | PEO (20M) | 1/5(4) | 1.2 |
| 27 | PEO (20M) | 4/1 | 0.85 |
| 28 | PEO (20M) | .5/1 | 1.3 |

(1)UV Absorbance at 296 nm
(2)Dry films cast from 20 microliter of a solution (50 percent ethanol) 0.25 percent by weight ESCALOL and polymer (concentration as indicated by ratio) on 3 cm$^2$ quartz surface.
(3)Comparative Example (No film-forming polymer present).
(4)Surprisingly, it was discovered that PEO (20M) and ESCALOL form a syneristic combination when employed in an amount such that the ratio by weight is at least about 1:10 of PEO (20M) to ESCALOL and not greater than about 20:1, preferably 1:5 to about 4:1.

EXAMPLES 29–33

The Compositions of Table IV were prepared as indicated in Table IV in a 50 percent ethanol solution and dry films cast on a flat quartz plate from 20 microliters of solution. The UV absorbance of each solution was measured.

Dry films were cast of the aforementioned compositions on an aluminum DSC specimen cup from 50 mi-

TABLE IV

| Example | Film-Forming Polymer | Conc. of[1] UV-Absorbing Material | UV-Absorbing Material | Conc. of[1] Films-Forming Polymer | Absorbance[2] |
|---|---|---|---|---|---|
| 29 | CALGON 502 | 1% | PABA | 1% | 1.2 |
| 30 | CROTEIN Q | 1% | PABA | 1% | 0.26 |
| 31 | METHOCEL | 0.5% | PABA | 0.5% | 1.2 |
| 32 | JR 400 | 0.5% | Ethyl PABA[3] | 0.5% | 0.6 |
| 33 | JR 400 | 1% | Ethyl PABA | 0.5% | 0.9 |

[1]Concentration expressed as weight percents.
[2]Absorbance of a dry film cast from 20 microliters of a solution (50 percent ethanol on 3 cm$^2$ planar quartz surface
[3]Absorbance of a dry film cast from 20 microliters of a solution (50 percent ethanol on 3 cm$^2$ planar quartz surface) had an absorbance of 0.08.

COMPARATIVE EXAMPLES 34–45

The potentiation of commercial sunscreening compositions was evaluated by adding a film-forming polymer to commercial sunscreening compositions as shown in Table V. In each case the addition of the film-forming polymer was observed to increase the UV absorbance of the sunscreening composition.

croliters of solution (100% ethanol a solvent containing about 0.5 or 1 percent by weight of 1-naphthyl-N-methylcarbamate) and the crystallinity of 1-napthyl-N-methylcarbamate in each composition determined by DSC. DSC showed almost the complete absence of a melting point at about 144° C. This is consistent with a fully dispersed topically active agent and formation of a microdispersion.

TABLE V

| Example | Commercial Product | UV-Absorbing Material | Conc. of UV-Absorbing Material[1] | Film-Forming Polymer | Conc. of Film-Forming Polymer | Absorbance |
|---|---|---|---|---|---|---|
| 34 | PRESUN (GEL)[2] | PABA | 0.5% | — | — | 0.3 |
| 35 | PRESUN (GEL) | PABA | 0.5% | JR-400 | 0.5% | 1.4 |
| 36 | PRESUN (GEL) | PABA | 0.5% | CELLOSIZE QP 300H | 0.5% | 1.4 |
| 37 | PRESUN (LOTION) | PABA | 0.5% | CELLOSIZE QP 300H | 0.5% | 1.3 |
| 38 | PRESUN (LOTION) | PABA | 0.5% | JR-400 | 0.5% | 2.2 |
| 39 | PRESUN (LOTION) | PABA | 0.5% | KLUCEL L | 0.5% | 1.3 |
| 40 | PRESUN (LOTION) | PABA | 0.5% | KLUCEL F | 0.5% | 0.70 |
| 41 | PRESUN (LOTION) | PABA | 0.5% | — | — | 0.16 |
| 42 | ROYAL HAWAIIAN[3] | PABA | 2.5% | — | — | 0.18 |
| 43 | ROYAL HAWAIIAN | PABA | 2.5% | JR-400 | 1.0% | 2.2 |
| 44 | PRESUN LOTION | PABA | 2.5% | — | — | 0.26 |
| 45 | PRESUN LOTION | PABA | 2.5% | JR-400 | 1.0% | 3.3 |

[1]Diluted from 5% PABA in commercial product to 0.5 percent by weight or 2.5 percent by weight as indicated (50 percent ethanol).
[2]PRESUN in the trademark of Westwood Phar. Inc. for sunscreening compositions containing 5 percent by weight PABA.
[3]ROYAL HAWAIIAN is the trademark of Royal Hawaiian Paba Corporation for sunscreening compositions containing 5 percent by weight PABA.

EXAMPLE 46

According to this invention a composition was prepared to demonstrate the invention when the topically active agent is an insecticide.

According to this invention, three compositions were prepared containing the insecticide 1-naphthyl-N-methyl carbamate and one each of the polymers of the group GANTREZ ES-225, HEC(QP33OH) and PEO(20M). The compositions had (film-forming polymer) to (1-naphthyl-N-methylcarbamate) weight ratios of 3:1 for HEC(QP33OH) and PEO(20M) and 4:1 for GANTREZ ES-225.

EXAMPLES 47–51

Additional compositions were prepared and analyzed similar to Example 46 for a variety of topically active agents. A weighed amount of a solution containing the topically active agent or topically active agent plus film-forming polymer was placed into an aluminum cup, covered and crystallinity determined by DSC. The film-forming polymer concentration was increased or decreased until a concentration of the polymer was found at which crystallization was inhibited as shown by failure to observe a melting point, with the results set forth in Table VI.

TABLE VI

| Example | Topical Activity | Evaporative Solvent | Topically Active Agent (wt. %) | Film-Forming Polymer (wt. %) | Weight Ratio of Polymer to Agent |
|---|---|---|---|---|---|
| 47 | Vitamin | Water | Ascorbic acid$^a$ (0.5%) | JR-400 (0.1%) | 0.2:1 |
| 48 | Preservative | Water | Germal$^b$ (0.5%) | JR-400 (0.5%) | 1:1 |
| 49 | Fungicide | Water | Omadine$^c$ (1%) | JR-400 (0.5%) | 0.5:1 |
| 50 | Germicide | Methanol/methyl | TCC$^d$ (0.5%) | Carbowax 6000 (0.5%) | 1:1 |

TABLE VI-continued

| Example | Topical Activity | Evaporative Solvent | Topically Active Agent (wt. %) | Film-Forming Polymer (wt. %) | Weight Ratio of Polymer to Agent |
|---|---|---|---|---|---|
| 51 | Insecticide | pyrrodidone Methanol/methyl pyrrodidone | IGR$^e$ (0.5%) | Carbowax 6000 (1.0%)b | 2:1 |

$^a$Surprisingly, it was discovered that Polymer JR and ascorbic acid (vitamin C) or a synergistic combination when employed in an amount such that the weight ratio is at least about 0.1:1 of polymer to agent, up to about 20:1, and preferably 0.2:1 to about 4:1.
$^b$N-(hydroxymethyl)-N-(1,3-dihydroxy-methyl-2,5-dioxo-4-imidazolidinyl-N'-hydroxymethyl urea.
$^c$Magnesium 1-hydroxy-2(1H)-pyridinethione.
$^d$N-(4-chlorophenyl)-N'-(3,4-dichlorophenyl)urea.
$^e$N-(1-chloro,2-methyl,3-β-chloronathyether benzyl)-N'-chlorobenzoyl urea.

What is claimed is:

1. A liquid, topical composition consisting essentially of an evaporative solvent and a film-forming polymer which is a cellulose, polyvinyl alcohol, polyvinyl pyrrolidone, polyether, polyester, water-soluble polyacrylamide or water-insoluble polyamide, which polymer is in solution with said solvent, said polymer in admixture with a topically effective amount of topically active agent in solution with said solvent, which is a crystalline material providing a uniform microdispersion characterized by the virtual absence of a melting point of said agent as measured by differential scanning calorimetry, wherein the weight ratio of polymer to agent is from about 1:1 to about 20:1 and is sufficient to provide for potentiation of an applied amount of said agent present as a substantially uniform microdispersion formed during the evaporation of said evaporative solvent to provide a dried film containing said polymer, characterized by a reduction in the agglomeration of said agent upon evaporation of the evaporative solvent and providing increased topical activity as compared to an equal amount of said agent applied when said film-forming polymer is absent.

2. The composition of claim 1 wherein the ratio of film-forming polymer to topically active agent is from about 1:1 to about 4:1.

3. The composition of claim 2 wherein the film-forming polymer is selected from the group consisting of: a quaternary ammonium cellulose derivative; a polymer of N,N-dimethyl 3,5-methylene piperidinium chloride; a copolymer of vinylpyrrolidone and dimethyl amino ethyl methacrylate quaternized with diethyl sulphate; a high molecular weight polymer of ethylene oxide; a polyethylene glycol polymer; a methyl ether of cellulose; a hydroxyethyl cellulose; a polyethylene glycol ester of fatty acid; a hydroxypropyl cellulose; a polyvinyl alcohol; a polypropylene glycol; an ester of polymethyl vinyl ether of maleic acid; and a cationic protein.

4. The composition of claim 3 wherein the topically active agent is selected from the group consisting of: para-amino benzoic acid or esters thereof; 1-naphthyl-N-methyl carbamate; ascorbic acid; N-(hydroxymethyl)-N-(1,3-dihydroxymethyl-2,5-dioxo-4-imidazolidinyl-N'-hydroxymethyl urea; magnesium 1-hydroxy-2(H)-pyridinethione; N-(4-chlorophenyl)-N'-(3,4-dichlorophenyl) urea; and N-(1-chloro, 2-methyl, 3-β-chloronaphthylether benzyl)-N'-chlorobenzoyl urea.

5. The composition of claim 4 wherein:
(a) the film-forming polymer is a quaternary nitrogen-substituted cellulose having the structure:

wherein $R_{cell}$ is a residue of an anhydroglucose unit, wheren Y is an integer having values 50 to 20,000, and wherein each R individually represents a substituent of the generic formula:

wherein the m is an integer having values from 0 to 10, n is an integer having values from 0 to 3, p is an integer having values from 0 to 10, and b is an integer having a value form 0 to 3 and the average value of n per anhydroglucose unit is from 0.1 to about 0.5 and the sum (m+p) is from about 0.8 to about 2; and (b) the topically active agent is para-amino benzoic acid or esters thereof; and (c) the evaporative solvent contains water, ethanol or mixtures thereof.

6. The composition of claims 1 or 2 wherein the topically active agent is an insecticide, a pesticide, a fungicide, a germicide, a vitamin or possesses activity on a microscopic or submicroscopic scale.

7. The composition of claims 6 wherein the topically active agent possesses activity on a microscopic or submicroscopic scale.

8. A light-sensitive composition according to claim 7 formed by selecting as the topically active agent a radiation selective material.

9. A sunscreening composition according to claim 8 formed by selecting as the topically active agent an ultraviolet light-absorbing material.

10. The sunscreen of claim 9 wherein the ultraviolet light-absorbing material is para-amino benzoic acid or esters thereof.

11. The composition of claim 1 wherein the evaporative solvent has a partial pressure at 25° C. of greater than than about 1 mm of mercury.

12. The composition of claim 11 wherein the evaporative solvent has a partial pressure at 25° C. of between about 10 mm to ab 250 mm of mercury.

13. The composition of claim 12 wherein the evaporative solvent is water or a lower alkanol.

14. The composition of claim 13 wherein the evaporative solvent is water, ethanol or mixtures thereof.

15. The composition of claim 1 wherein the film forming polymer is a cellulose or polyethylene oxide.

16. The composition of claim 15 wherein the film-forming polymer is a quaternary nitrogen-substituted cellulose having the structure wherein $R_{cell}$ is a residue of an anhydroglucose unit, wherein Y is an integer having values 50 to 20,000, and wherein each R individually represents a substituent of the generic formula:

wherein the m is an integer having values from 0 to 10, n is an integer having values from 0 to 3, p is an integer having values from 0 to 10, and b is an integer having a value form 0 to 3 and the average value of n per anhydroglucose unit is from 0.1 to about 0.5 and the sum (m+p) is from about 0.8 to about 2.

17. A liquid, topical composition comprising an evaporative solvent and a film-forming polymer which is a cellulose polyvinyl alcohol, polyvinyl pyrrolidone, polyether, polyester, water-soluble polyacrylamide or water-insoluble polyamide, which polymer is in solution with a topically effective amount of topically active agent wherein the improvement comprises providing said film-forming polymer in an amount such that the weight ratio of polymer to agent is from about 1:1 to about 20:1 and is sufficient to provide for potentiation of an applied amount of said agent by enhancing the activity of said agent in a dried film to a substantially greater level than the activity of a corresponding amount of said agent in a dried film wherein said polymer is absent.

18. The composition of claim 17 wherein said potentiation provides greater than a 100% increase in topically active agent in-vitro activity.

19. The composition of claim 18 wherein said potentiation provides between a 500% to 50,000% increase in topically active agent in-vitro activity.

20. The composition of claim 17 wherein:
(a) the film-forming polymer is a quaternary nitrogen-substituted cellulose having the structure:

wherein $R_{cell}$ is a residue of an anhydroglucose unit, wherein Y is an integer having values 50 to 20,000, and wherein each R individually represents a substituent of the generic formula:

wherein the m is an integer having values from 0 to 10, n is an integer having values from 0 to 3, p is an integer having values from 0 to 10, and b is an integer having a value form 0 to 3 and the average value of n per anhydroglucose unit is from 0.1 to about 0.5 and the sum (m+p) is from about 0.8 to about 2; and (b) the topically active agent is para-amino benzoic acid or esters thereof; and

(c) the evaporative solvent contains water, ethanol or mixtures thereof.

21. A dry cast film comprising a substantially uniform microdispersion of a topically effective amount of topically active agent, which is a crystalline material providing a uniform microdispersion characterized by the virtual absence of a melting point of said agent as measured by differential scanning calorimetry, in a film containing film-forming polymer which is a cellulose, polyvinyl alcohol, polyvinyl pyrrolidone, polyether, polyester, water-soluble polyacrylamide or water-insoluble polyamide, wherein the weight ratio of said polymer to said agent is from about 1:1 to about 20:1, characterized by a reduction in the agglomeration of said agent upon evaporation of said solvent when said polymer is present as compared to when said polymer is absent.

22. The composition of claim 21 wherein:
(a) the film-forming polymer is a quaternary nitrogen-substituted cellulose having the structure wherein $R_{cell}$ is a residue of an anhydroglucose unit, wherein Y is an integer having values 50 to 20,000, and wherein each R individually represents a substituent of the generic formula:

wherein the m is an integer having values from 0 to 10, n is an integer having values from 0 to 3, p is an integer having values from 0 to 10, and b is an integer having a value form 0 to 3 and the average value of n per anhydroglucose unit is from 0.1 to about 0.5 and the sum (m+p) is from about 0.8 to about 2; and (b) the topically active agent is para-amino benzoic acid or esters thereof; and (c) the evaporative solvent contains water, ethanol or mixtures thereof.

23. A process for potentiating an applied amount of a topically active agent, which is a crystalline material providing a uniform microdispersion characterized by the virtual absence of a melting point of said agent as measured by differential scanning calorimetry, which comprises:
(1) directly applying a liquid, topical composition consisting essentially of an evaporative solvent and a film-forming polymer which is a cellulose, polyvinyl alcohol, polyvinyl pyrrolidone, polyether, polyester, water-soluble polyacrylamide or water-insoluble polyamide, which polymer is in solution with said solvent, said polymer in admixture with a topically effective amount of said agent wherein the weight ratio of said polymer to said agent is from about 1:1 to about 20:1, to a surface; and
(2) evaporating off said solvent to a melting point of said ascorbic acid as measured by differential scanning calorimetry, wherein the weight ratio of said polymer to ascorbic acid is from about 0.1:1 to about 20:1 and is sufficient to provide for potentiation of an applied amount of said ascorbic acid present as a substantially uniform microdispersion in a dried film containing said polymer, characterized by a reduction in the agglomeration of said agent upon evaporation of said solvent when said polymer is present as compared to when said polymer is absent.

36. A liquid, topical composition consisting essentially of an evaporative solvent and a polyethylene oxide in solution with said solvent, said polymer in admixture with a topically effective amount of 2-ethylhexyl para-diethylamino benzoate, which is a crystalline material providing a uniform microdispersion characterized by the virtual absence of a melting point of said 2-ethylhexyl-para-diethylamino benzoate as measured by differential scanning calorimetry, wherein the weight ratio of polymer to benzoate is from about 0.1:1 to about 20:1 and is sufficient to provide for potentiation of an applied amount of said benzoate present as a substantially uniform microdispersion in a dried film containing said polymer, characterized by a reduction in the agglomeration of said agent upon evaporation of said solvent when said polymer is present as compared to when said polymer is absent.

* * * * *

UNITED STATES PATENT AND TRADEMARK OFFICE
CERTIFICATE OF CORRECTION

PATENT NO. : 4,938,951

DATED : 3 July 1990

INVENTOR(S) : Leung et al.

It is certified that error appears in the above-identified patent and that said Letters Patent is hereby corrected as shown below:

Column 3, line 26, change "absorbence" to -- absorbance --.
Column 9, line 19, change "AP" to -- QP --. Column 12, line 60, change "syneristic" to -- synergistic --. Column 15, line 17 (in footnote "e" of Table VI), change "chloronathylether" to -- chloronapthylether --. Column 16 at line 30, column 18 at lines 5 and 53, column 19 at line 63, column 20 at line 45 (the first line of the second formula in Claims 5, 20, 22, 31 and 34, respectively) after "$H_{2b}$", insert -- 0 --. Column 17, line 41 (line 6 of claim 17) after "with", insert -- said solvent, said polymer in admixture --.

Signed and Sealed this

Twenty-seventh Day of April, 1993

Attest:

MICHAEL K. KIRK

*Attesting Officer*    *Acting Commissioner of Patents and Trademarks*